United States Patent
Yamamoto et al.

(10) Patent No.: US 10,051,722 B2
(45) Date of Patent: Aug. 14, 2018

(54) SYNCHROTRON INJECTOR SYSTEM AND OPERATING METHOD FOR DRIFT TUBE LINEAR ACCELERATOR

(71) Applicant: MITSUBISHI ELECTRIC CORPORATION, Chiyoda-ku, Tokyo (JP)

(72) Inventors: Kazuo Yamamoto, Tokyo (JP); Sadahiro Kawasaki, Tokyo (JP); Hiromitsu Inoue, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 15/553,410

(22) PCT Filed: Jul. 10, 2015

(86) PCT No.: PCT/JP2015/069844
§ 371 (c)(1),
(2) Date: Aug. 24, 2017

(87) PCT Pub. No.: WO2016/135998
PCT Pub. Date: Sep. 1, 2016

(65) Prior Publication Data
US 2018/0092197 A1   Mar. 29, 2018

(30) Foreign Application Priority Data

Feb. 25, 2015   (WO) .................. PCT/JP2015/055385

(51) Int. Cl.
*H05H 13/04*   (2006.01)
*H05H 7/02*    (2006.01)
(Continued)

(52) U.S. Cl.
CPC .............. *H05H 13/04* (2013.01); *H05H 7/02* (2013.01); *H05H 7/08* (2013.01); *H05H 7/22* (2013.01);
(Continued)

(58) Field of Classification Search
None
See application file for complete search history.

(56) References Cited

U.S. PATENT DOCUMENTS

| | | | |
|---|---|---|---|
| 6,617,810 B2 * | 9/2003 | Symons | H05H 7/18 250/292 |
| 6,777,893 B1 * | 8/2004 | Swenson | H05H 7/22 315/505 |

(Continued)

FOREIGN PATENT DOCUMENTS

| | | |
|---|---|---|
| JP | 2001-085198 A | 3/2001 |
| JP | 2006-310013 A | 11/2006 |

(Continued)

OTHER PUBLICATIONS

International Search Report (PCT/ISA/210) dated Sep. 15, 2015, by the Japanese Patent Office as the International Searching Authority for International Application No. PCT/JP2015/069844.

(Continued)

*Primary Examiner* — Douglas W Owens
*Assistant Examiner* — Srinivas Sathiraju
(74) *Attorney, Agent, or Firm* — Buchanan Ingersoll & Rooney PC

(57) ABSTRACT

When accelerating first ions, radio frequency power is fed to a drift tube linear accelerator so that the phase difference between an accelerating half cycle for accelerating the first ions in one of the plurality of drift tube gaps and the accelerating half cycle for accelerating the accelerated first ions reaching the next drift tube gap is set to a first (Continued)

accelerating cycle phase difference; and when accelerating second ions having a charge-to-mass ratio lower than the first ions, the radio frequency power is fed to the drift tube linear accelerator so that the phase difference between an accelerating half cycle for accelerating the second ions in the one drift tube gap and the accelerating half cycle for the accelerated second ions reaching the next drift tube gap is set to a second accelerating cycle phase difference that is larger than the first accelerating cycle phase difference.

10 Claims, 12 Drawing Sheets

(51) Int. Cl.
  *H05H 7/22* (2006.01)
  *H05H 7/08* (2006.01)
  *H05H 9/04* (2006.01)
(52) U.S. Cl.
  CPC ....... *H05H 9/042* (2013.01); *H05H 2007/025* (2013.01); *H05H 2007/082* (2013.01); *H05H 2007/222* (2013.01); *H05H 2007/225* (2013.01)

(56) References Cited

U.S. PATENT DOCUMENTS

| | | | | |
|---|---|---|---|---|
| 6,855,942 B2* | 2/2005 | Bechthold | ................ | G21K 5/04 250/492.21 |
| 6,914,396 B1* | 7/2005 | Symons | ................... | H05H 9/00 250/292 |
| 7,432,516 B2* | 10/2008 | Peggs | .................... | H05H 13/04 250/281 |
| 7,547,878 B2* | 6/2009 | Schultz | ................ | G01N 27/622 250/281 |
| 8,294,088 B2* | 10/2012 | Pringle | .................... | H01J 47/02 250/283 |
| 8,299,443 B1* | 10/2012 | Shvartsburg | .......... | H01J 49/066 250/292 |
| 8,384,023 B2* | 2/2013 | Schultz | ............... | H01J 49/0045 250/287 |
| 8,405,056 B2* | 3/2013 | Amaldi | .................... | A61N 5/10 250/396 R |
| 8,836,247 B2* | 9/2014 | Yamamoto | ............. | H05H 9/042 315/500 |
| 9,386,683 B2* | 7/2016 | Kakutani | ............. | A61N 5/1077 |
| 9,402,298 B2* | 7/2016 | Sugahara | ................. | A61N 5/10 |
| 2009/0195194 A1 | 8/2009 | Takayama et al. | | |
| 2013/0038248 A1 | 2/2013 | Yamamoto et al. | | |
| 2016/0249444 A1 | 8/2016 | Yamamoto et al. | | |

FOREIGN PATENT DOCUMENTS

| JP | 2009-217938 A | 9/2009 |
|---|---|---|
| WO | WO 2012/008255 A1 | 1/2012 |
| WO | WO 2015/079487 A1 | 6/2015 |

OTHER PUBLICATIONS

Written Opinion (PCT/ISA/237) dated Sep. 15, 2015, by the Japanese Patent Office as the International Searching Authority for International Application No. PCT/JP2015/069844.

* cited by examiner

SYNCHROTRON INJECTOR SYSTEM AND OPERATING METHOD FOR DRIFT TUBE LINEAR ACCELERATOR

TECHNICAL FIELD

The present invention relates to a synchrotron injector system for injecting different kinds of ions into a synchrotron to allow the different kinds of ions to be accelerated in one synchrotron accelerator system.

BACKGROUND ART

A particle beam that is flux of high-energy charged particles accelerated by and extracted from a synchrotron has been utilized in, for example, cancer treatment. It may be preferable in some particle beam treatments to select a kind of particle beam depending on a treatment target. For that reason, it is desired that different kinds of particle beams can be extracted from one synchrotron accelerator system. Since synchrotrons are for accelerating injected charged particles, i.e., ions, a synchrotron injector system is needed that injects different kinds of ions into a synchrotron so as to allow the different kinds of ions to be extracted from the synchrotron.

Patent Document 1 discloses a technology enabling all kinds of ions to be accelerated to given energy levels by one synchrotron. However, regarding the injector system for injecting the ions into the synchrotron, it only states that the ion beams to be injected are accelerated to a certain energy level by a pre-accelerator.

Moreover, Patent Document 2 describes that respective ion sources are necessary for generating a proton beam and a carbon beam to utilize both beams; however, no detail description is made about the pre-accelerator for injecting both ion beams into the synchrotron.

Furthermore, Patent Document 3 discloses a configuration of an APF-IH drift-tube linear accelerator that is capable of accelerating a particle beam such as a large current proton beam.

PRIOR ART DOCUMENT

Patent Document
Patent Document 1: JP2006-310013 A;
Patent Document 2: JP2009-217938 A; and
Patent Document 3: WO2012/008255 A1.

SUMMARY OF THE INVENTION

Problem that the Invention is to Solve

In a synchrotron injector system for pre-accelerating different kinds of ions such as, for example, protons and carbon ions to a level for a synchrotron to be able to accelerate, the different kinds of ions are accelerated to the same energy level, as described in, for example, Patent Document 1. A conventional synchrotron injector system is thus restricted to conditions in which both kinds of ions are pre-accelerated to the same energy level by one accelerator. Such a conventional injector system is inefficient and large in size since its pre-acceleration energy is not optimal for each kind of ions. Since high charge-to-mass ratio (charge/mass) ions (for example, the protons:charge/mass=1/1) are largely subject to space charge effect, the energy for injecting the high charge-to-mass ions into a synchrotron is desired to be larger than that for injecting a low charge-to-mass ratio ions (for example, the tetravalent carbon ions: charge/mass=4/12). Contrarily, since a higher accelerating voltage is necessary to accelerate the low charge-to-mass ratio ions than to accelerate the high charge-to-mass ratio ions and a large accelerator is required accordingly, the energy for injecting the low charge-to-mass ratio ions into the synchrotron is desired to be lower than that for injecting the high charge-to-mass ratio ions. Conventionally, since the above desires has not been satisfied, the injection energy for a synchrotron is fixed to the same regardless of whether the charge-to-mass ratio of the ions is high or low and the accelerator is large in size.

The present invention is made to eliminate such the foregoing problems with the conventional synchrotron injector systems and aimed at providing a compact synchrotron injector system that is capable of accelerating different kinds of ions.

Means for Solving the Problems

A synchrotron injector system according to the present invention includes a first ion source for generating first ions; a second ion source for generating second ions having a charge-to-mass ratio ($q2/A2$) lower than the charge-to-mass ratio ($q1/A1$) of the first ions; a drift tube linear accelerator having: a cylindrical resonator; and a plurality of drift tubes arranged linearly along the center axis of the cylindrical resonator, to accelerate either the first ions or the second ions in an accelerating half cycle that is a radio frequency half cycle containing an accelerating phase of radio frequency electric fields produced in a plurality of drift tube gaps formed between the plurality of drift tubes; a radio frequency generator for feeding radio frequency power to the drift tube linear accelerator; and a low-energy beam delivery line for injecting either the first ions or the second ions into the drift tube linear accelerator, wherein when the first ions are injected from the low-energy beam delivery line, the radio frequency generator fed the radio frequency power to the drift tube linear accelerator so that the phase difference between an accelerating half cycle for accelerating the first ions in one drift tube gap of the plurality of drift tube gaps and an accelerating half cycle for accelerating the accelerated first ions reaching the next drift tube gap is set to a first accelerating cycle phase difference and when the second ions are injected from the low-energy beam delivery line, the radio frequency power is fed to the drift tube linear accelerator so that the phase difference between an accelerating half cycle for accelerating the second ions in the one drift tube gap and an accelerating half cycle for the accelerated second ions reaching the next drift tube gap is set to a second accelerating cycle phase difference that is larger than the first accelerating cycle phase difference.

An operating method according to the present invention for the drift-tube linear accelerator that includes a cylindrical resonator and a plurality of drift tubes arranged linearly along the center axis of the cylindrical resonator to accelerate either first ions or second ions having a charge-to-mass ratio ($q2/A2$) lower than the charge-to-mass ratio ($q1/A1$) of the first ions in an accelerating half cycle that is a radio frequency half cycle containing an accelerating phase of radio frequency electric fields produced in a plurality of drift tube gaps formed between the plurality of drift tubes, enable the drift-tube linear accelerator to operate so that when accelerating the first ions, radio frequency power is fed the radio frequency power to the drift tube linear accelerator so that the phase difference between an accelerating half cycle for accelerating the first ions in one drift tube gap of the plurality of drift tube gaps and an accelerating half cycle for accelerating the accelerated first ions reaching the next drift tube gap is set to be a first accelerating cycle phase difference and when accelerating the first ions, the radio frequency power is fed to the drift tube linear accelerator so that the phase difference between an accelerating half cycle for accelerating the second ions in the one drift tube gap and an accelerating half cycle for the accelerated second ions reaching the next drift tube gap is set to a second accelerating cycle phase difference that is larger than the first accelerating cycle phase difference.

Advantage of the Invention

According to the present invention, a synchrotron injector system can be provided that is made compact and capable of injecting different kinds of ions for these ions to be extracted from a synchrotron with different energies.

EMBODIMENTS FOR CARRYING OUT THE INVENTION

In synchrotron injector systems, a larger power needs to accelerate heavy ions than to accelerate light ions. Accordingly, in order to be able to accelerate different kinds of ions, for example, protons and carbon ions, an accelerator is designed first that accelerates heavy ions, i.e., the carbon ions, to a necessary energy level. And based on the idea that the light protons can be accelerated to the same energy level as the carbon ions by reducing the power fed to the accelerator which accelerates the carbon ions up to the necessary energy level, a conventional injector system was constructed that accelerates the carbon ions and the protons to the same energy level to inject. However, the injection energy for a synchrotron is preferably set higher for high charge-to-mass-ratio ions such as the protons than for low charge-to-mass ratio ions such as the carbon ions. Conventionally, since a priority has been placed on acceleration of the heavy carbon ions in designing injector systems, there has been no idea of realizing an injector system that is provided with one accelerator for injecting the carbon ions and the protons with different energies.

In contrast to that, the present invention realizes an injection system for accelerating different kinds of ions to energy levels different from each other by abandoning the conventional idea that the injector system optimized for the low charge-to-mass ratio ions is also used for accelerating the high charge-to-mass ratio ions, instead based on an opposite that an injector system accelerating the high charge-to-mass ratio ions to an energy level optimized for injecting into a synchrotron is used in accelerating the lower charge-to-mass ratio ions. This idea enables an injector system to be realized in a small size that is capable of injecting high charge-to-mass ratio ions and low charge-to-mass ratio ions with energies respectively optimal for a synchrotron. Hereinafter, the present invention is described in the following embodiments.

Embodiment 1

Figure 1:
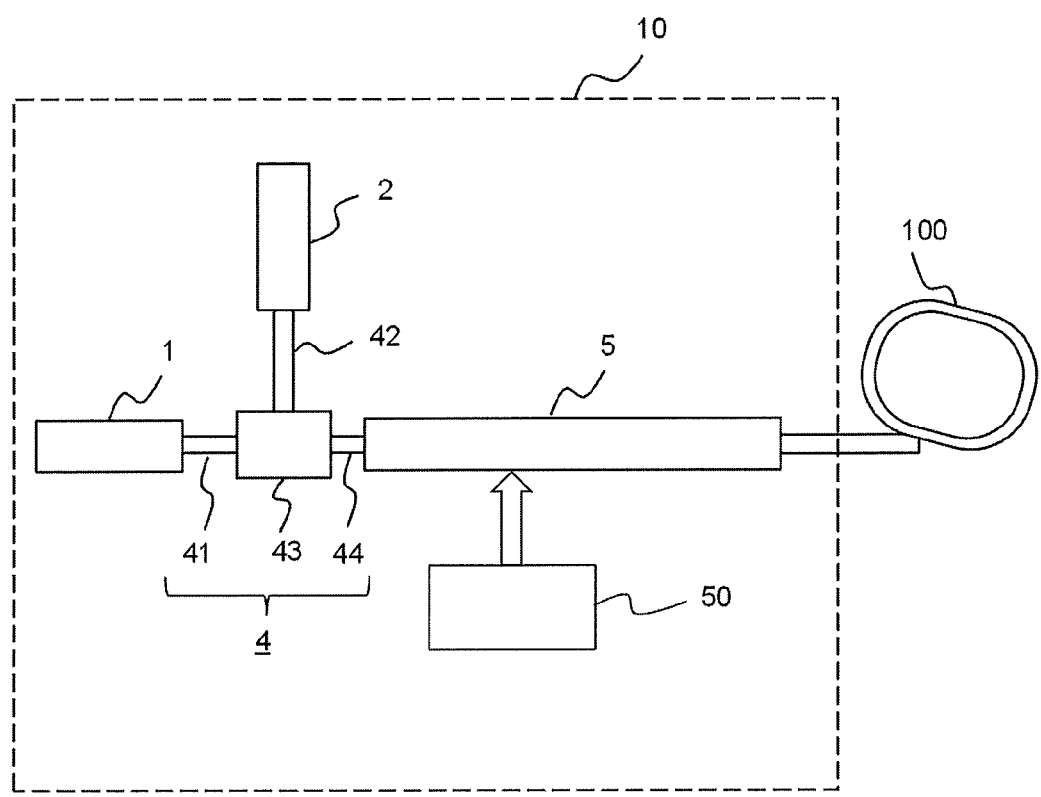
FIG. 1 is a block diagram showing a configuration of a synchrotron injector system according to Embodiment 1 of the present invention.

FIG. 1 is a block diagram schematically showing a configuration of a synchrotron injector system according to Embodiment 1 of the present invention. The synchrotron injector system 10 is capable of switchingly injecting two kinds of ions into a synchrotron 100. The synchrotron injector system 10 includes a first ion source 1 for generating first ions and a second ion source 2 for generating second ions having a charge-to-mass ratio lower than the first ions. The following description is made taking an example that uses the protons as the first ions and tetravalent carbon ions as the second ions. It should be noted that the present invention can be applied to a combination of various ions on condition that the charge-to-mass ratio (q2/A2) of the second ions is lower than the charge-to-mass ratio (q1/A1) of the first ions, for example, to a combination such as of the protons (charge-to-mass ratio=1) used as the first ions and monovalent helium ions (charge-to-mass ratio=1/4) used as the second ions, and of helium ions as the first ions and carbon ions as the second ions.

The charge q of the proton is monovalent, and defining its mass A to be one, the charge-to-mass ratio q/A of the proton is 1/1; and the charge of the carbon ion is tetravalent and since its mass is 12 relative to the proton's mass being one, the charge-to-mass ratio of the carbon ion is 4/12. That is, the charge-to-mass ratio of the carbon ion is lower than that of the proton. The protons generated in the first ion source 1 and the carbon ions generated in the second ion source 2 pass through a first low-energy beam delivery line 41 and a second low-energy beam delivery line 42, respectively, to be injected into a beam line merging device 43. The beam line merging device 43 is configured to merge the first low-energy beam delivery line 41 and the second low-energy beam delivery line 42 into one beam delivery line 44 and to switch over the protons and the carbon ions for either of them to be injected into a drift tube linear accelerator 5. The beam delivery line for the protons injected from the first ion source 1 into the drift tube linear accelerator 5 and that for the carbon ions injected from the second ion source 2 into the drift tube linear accelerator 5 are collectively referred to as a low-energy beam delivery line 4.

The beam line merging device 43 deflects the carbon ions injected from the second ion source 2 to merge them into the beam delivery line 44. The carbon ions injected from the second ion source 2 consist of carbon ions having different valences including tetravalent carbon ions. The accelerator accelerates only the tetravalent carbon ions. For that reason, the beam line merging device 43 is configured to deflect the carbon ions from the second ion source 2 to merge only tetravalent carbon ions into the beam delivery line 44.

Figure 2:
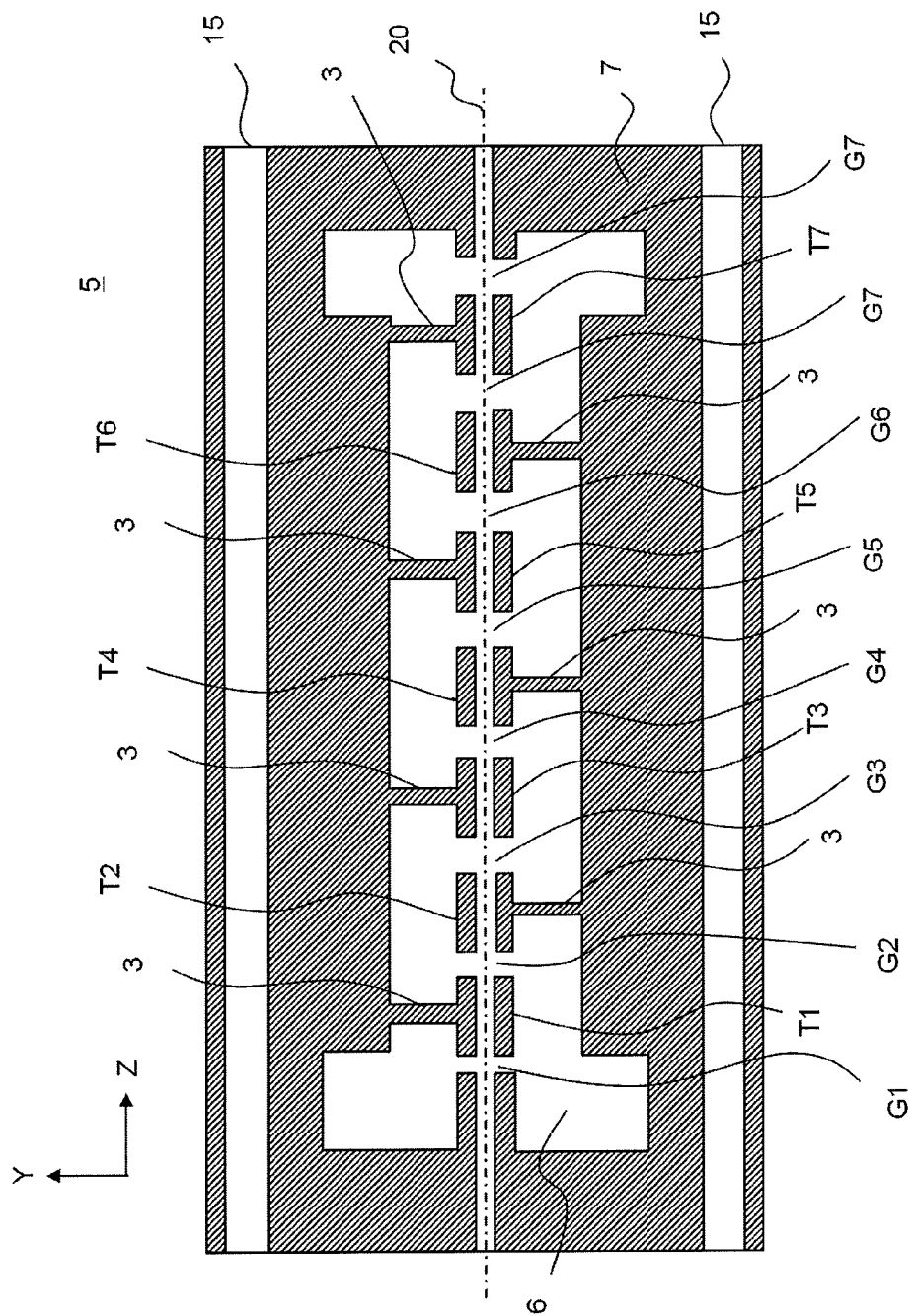
FIG. 2 is a side cross-sectional view schematically showing the configuration of the drift tube linear accelerator of the synchrotron injector system according to Embodiment 1 of the present invention.

FIG. 2 is a side cross-sectional view schematically showing the configuration of the drift tube linear accelerator 5 in the synchrotron injector system according to Embodiment 1 of the present invention. The drift tube linear accelerator 5 includes a plurality of drift tubes T1, T2 . . . arranged inside its cylindrical resonator 6 in the cylindrical axial direction thereof. While the arrangement of seven drift tubes is shown in FIG. 2 for simplicity, more drift tubes are arranged in many cases. The inside of the cylindrical resonator 6 is maintained under vacuum. Each drift tube has a cylindrical shape with a center through hole aligned with the acceleration axis 20 along which the ions travel and is supported by a stem 3 fixed to the wall 7 of the cylindrical resonator. In the drift tube linear accelerator shown in FIG. 2, the stems of the adjacent drift tubes extend opposite to each other. A drift tube linear accelerator with such a configuration is called an interdigital-H (IH) drift-tube linear accelerator. In the drift tube linear accelerator, the radio frequency power is fed into the cylindrical resonator from a radio frequency generator 50 to produce radio frequency electric fields in gaps G1, G2, . . . between the adjacent drift tubes (hereinafter, referred to as drift tube gaps). The ions traveling along the acceleration axis 20 are accelerated by the radio frequency electric fields.

The ions are accelerated as a particle beam. Since the particle beam consists of bunches of the ions (charged particles), a diverging force acts between each other of the particles (this refers to as "space charge effect"). Consequently, the particles diverge in both radial and traveling directions as they travel in the traveling direction. In particular, the radial divergence causes loss of the particles due to collision with the vacuum duct wall. Hence, there are needed radially converging devices for suppressing the radial divergence of the beam. In contrast to this, a drift tube linear accelerator called an alternating-phase-focusing interdigital-H (APF-IH) drift-tube linear accelerator needs no radially converging device since the APF-IH linear accelerator is designed so that a curved electric field distribution produced in the drift tube gaps and the timing for the particle beam to pass therethrough are coupled to obtain beam converging forces.

Figure 3:
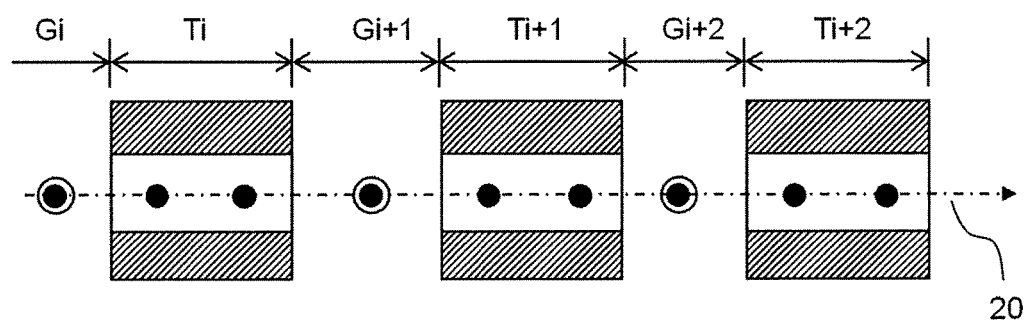
FIG. 3 is a schematic diagram illustrating traveling of ions while accelerated in the drift-tube gaps.

FIG. 3 is a schematic diagram illustrating traveling of ions while accelerated in the drift-tube gaps. The ion particles travel from left to right in FIG. 3 along the acceleration axis 20. The ion particles are accelerated in an i-th drift tube gap Gi, then travels through the drift tube Ti without accelerated, and then are accelerated in the next drift tube gap Gi+1. Likewise, the ion particles travel through the drift tube Ti+1 without accelerated, and then are accelerated in the further next drift tube gap Gi+2. In this way, the ion particles are accelerated every time it passes through the drift tube gaps. In FIG. 3, the ion particles subjected to the acceleration are diagrammatically indicated by the double circles and those traveling without subjected to the acceleration, by the black circles, respectively.

Figure 4:
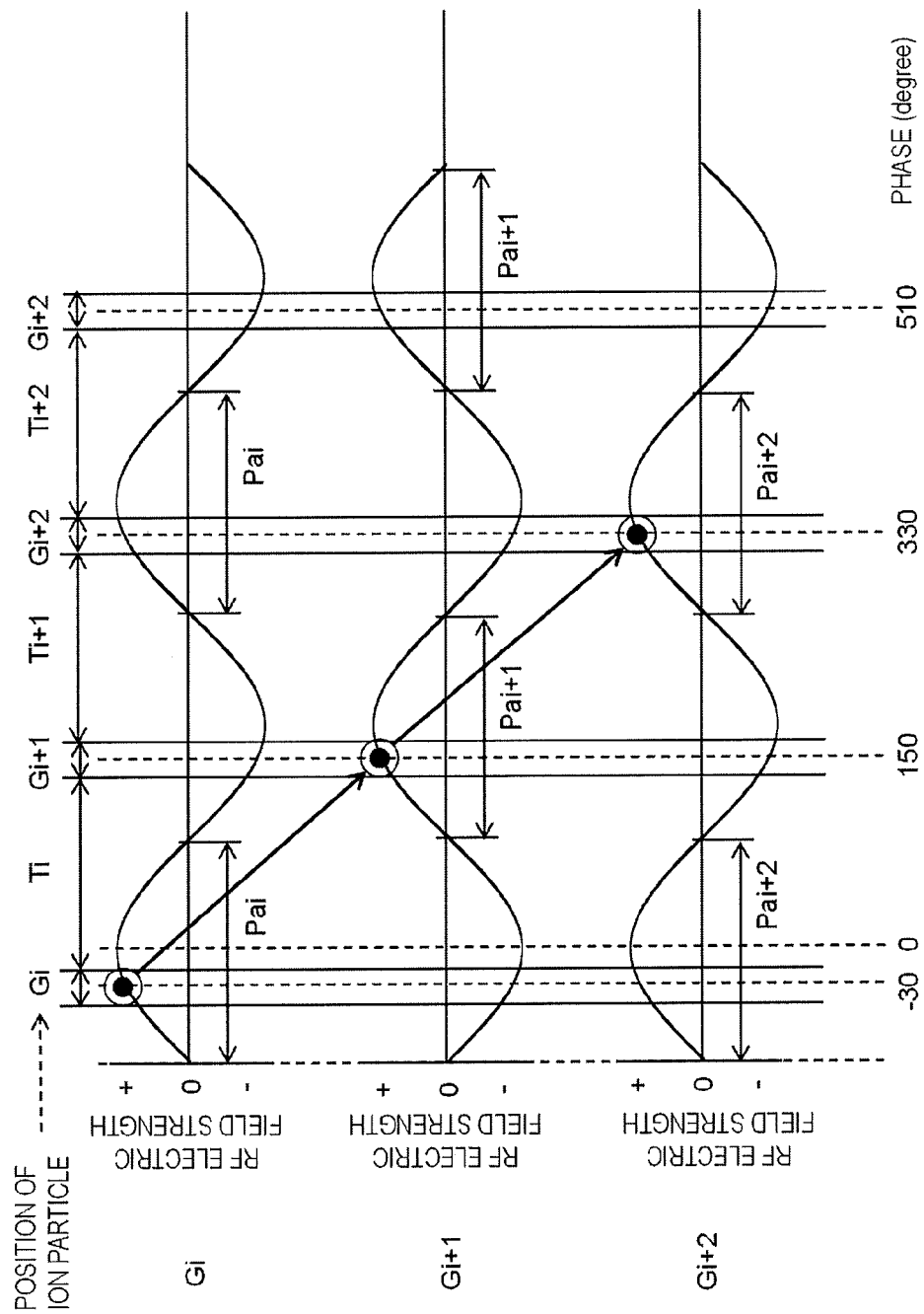
FIG. 4 is a diagrammatic chart illustrating an operation of accelerating first ions in the drift tube linear accelerator in the synchrotron injector system according to Embodiment 1 of the present invention.

An ion particle accelerating operation of the IH drift-tube linear accelerator is briefly explained with reference to FIG. 4. FIG. 4 is a diagrammatic chart illustrating how the ion particles are accelerated sequentially in the drift tube gaps Gi, Gi+1, Gi+2, . . . while passing therethrough. The horizontal axes represent phases of the radio frequency electric fields and also represent time because advancing of phase means elapsing of time, in other words, time elapses in right direction of the horizontal axes. In the respective drift tube gaps, radio frequency electric fields are produced in accordance with the radio frequency power fed into the cylindrical resonator. Each radio frequency electric field strength varies as a sine curve as shown in FIG. 4. In FIG. 4, the phase values are written relative to the peak phase of the radio frequency electric field strength produced in the drift tube Gi being defined as 0 degrees. The IH drift-tube linear accelerator is designed so that the radio frequency electric fields to be produced in adjacent drift tube gaps have phases opposite to each other, as illustrated by the radio frequency electric field strengths produced in the drift tube gaps Gi, Gi+1 and Gi+1, Gi+2 shown in FIG. 4. Note that in FIG. 4, the radio frequency electric field direction to accelerate the ions is defined to be positive (above each horizontal axes). Since the ions can be accelerated only when the radio frequency electric field strength is positive, the half cycle during the positive radio frequency electric field strength is here referred to as an accelerating half cycle. The acceleration half cycle Pai in the drift tube gap Gi and the accelerating half cycle Pai+2 in the drift tube gap Gi+2 have ranges such as from −90 to +90 degrees and from 270 to 450 degrees, respectively, i.e., the half cycle period has a range from (360*N−90) degrees to (360*N+90) degrees. Likewise, the accelerating half cycle Pai+1 in the drift tube gap Gi+1 has a range from (360*N+90) to (360*N+270) degrees. Here, N is an integer including zero.

The double circles represent the position of ion particles as the phase advances, in other words, as time advances, and the arrows represent traveling of the ion particles to the position. The uppermost part of FIG. 4 shows the position of each section of the drift-tube linear accelerator to help indicate in which section the ion particles exist at a phase of the radio frequency, i.e., at a time corresponding to the phase. The ion particles are accelerated in the drift tube gap Gi by receiving energy from the radio frequency electric field produced in the drift tube gap Gi. When the ion particles enter into the drift tube Ti, they are subjected to no acceleration and travel with their energy being kept intact and then further accelerated in the next drift tube gap Gi+1 by receiving energy from the radio frequency electric field produced in the drift tube gap Gi+1. Traveling of the ion particles while accelerated in this way is illustrated in FIG. 4.

In the IH drift-tube linear accelerator, the electric field strength is typically adjusted for the ion particles to pass through a drift tube gap at a phase shortly before the electric field strength peaks in an accelerating half cycle, for example, at a phase around −30 degrees from the peak of the electric field strength in the drift tube gap Gi as shown in FIG. 4. This forms a bunch of ion particles because the ion particles passing a little later through the gap are more accelerated. In the IH drift-tube linear accelerator, since the radio frequency electric field having an opposite phase is produced at the next drift tube gap, the accelerating half cycle Pai+1 at the drift tube gap Gi+1 is delayed by half the cycle from the accelerating half cycle Pai at the drift tube gap Gi. That is, the phase difference between the accelerating half cycles at the adjacent drift-tube gaps is half the cycle. The drift tube linear accelerator is designed for the bunch of ions to pass through the drift tube gap Gi+1 a little before the radio frequency electric field strength in the accelerating half cycle reaches its peak, more specifically, at a phase around 150 degrees. In this way, the bunch of ions is accelerated every time it passes through the drift tubes.

A conventional IH drift-tube linear accelerator is designed as described above. During operation, the radio frequency power is fed so that the accelerating operation is performed in accordance with the design to accelerate the bunch of ion particles, i.e., the ion beam, whereby the ion beam having a design energy is injected into the synchrotron 100. In Embodiment 1 of the present invention, the first ions having a high charge-to-mass ratio (for example, the protons) are accelerated by the same operation as with the conventional one illustrated in FIG. 4. In a case of accelerating the second ions having a low charge-to-mass ratio (for example, the tetravalent carbon ions), however, the phase difference between the accelerating half cycles in adjacent drift tube gaps is set larger than that between the accelerating half cycles for the first ions. Here, the phase difference between the accelerating half cycles in which the first ions are accelerated in adjacent drift tube gaps is referred to as a first accelerating cycle phase difference and the phase difference between the accelerating half cycles in which the second ions are accelerated in the adjacent drift tube gaps is referred to as a second accelerating cycle phase difference. In the above operation, the first accelerating cycle phase difference is half the cycle (0.5 cycles).

Figure 5:
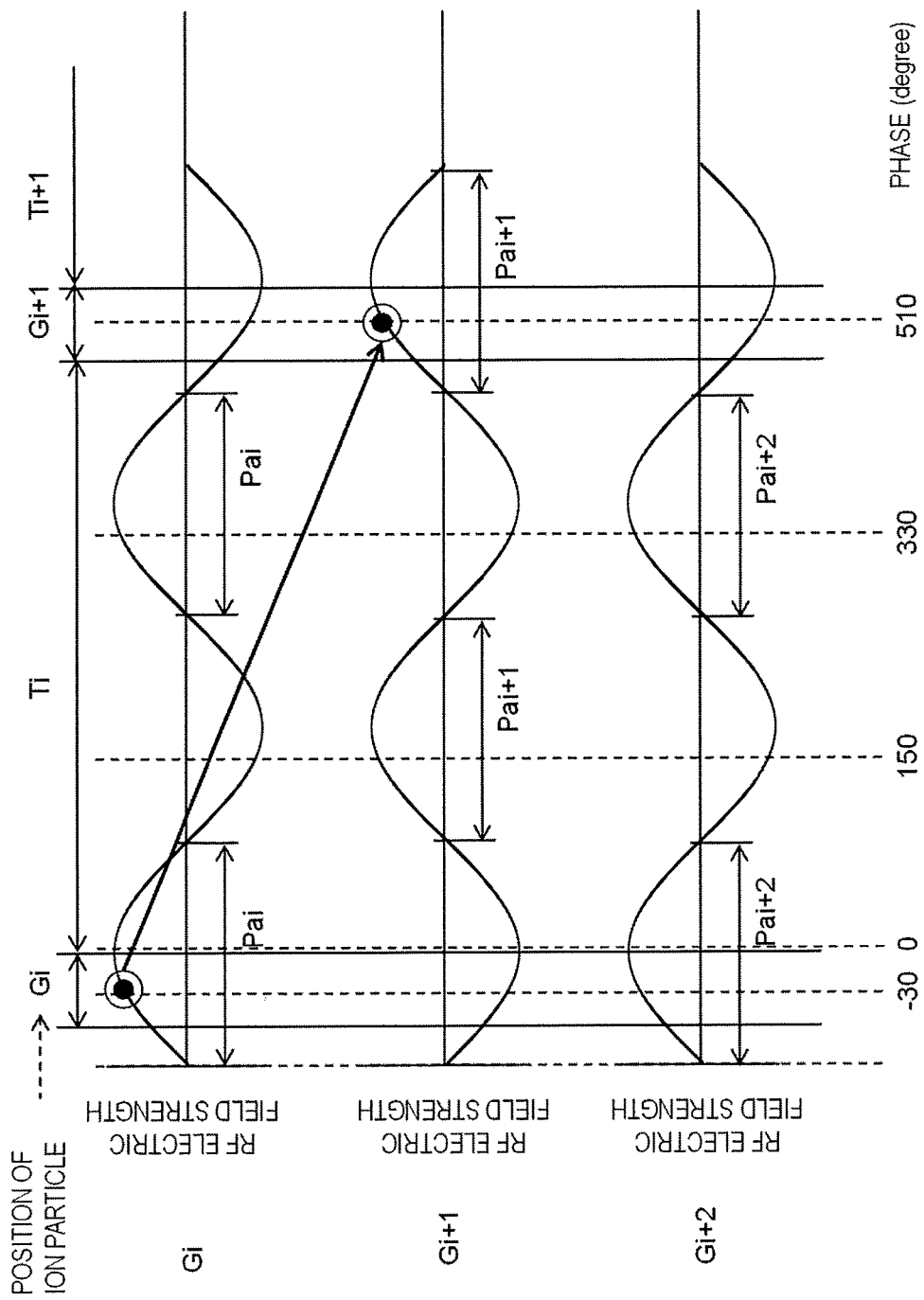
FIG. 5 is a diagrammatic chart illustrating an operation of accelerating second ions in the drift tube linear accelerator in the synchrotron injector system according to Embodiment 1 of the present invention.

FIG. 5 is a diagram illustrating how the drift tube linear accelerator in the synchrotron injector system according to the present invention accelerates the second ions of the tetravalent carbon ions. The bunch of second ions is accelerated when passing through the drift tube gap Gi at a phase around −30 degrees. The radio frequency electric field strength, i.e., the radio frequency power fed into the cylindrical resonator, is adjusted so that the ion beam is accelerated in the drift tube gap Gi+1 not at a phase in the next accelerating half cycle but at a phase around 510 degrees in the further next half cycle that is the accelerating half cycle delayed by one cycle from the next half cycle. In the above operation, the second accelerating cycle phase difference is 1.5 cycles. By such the accelerating operation, the second ions are accelerated to a velocity lower than the first ions. In other words, the energy of the second ions injected from the drift tube linear accelerator is lower than that of the first ions. Representing the charge and mass of the first ion and the charge and mass of the second ion by q1, A1, and q2, A2, respectively, the injection energy of the second ions is preferably set to a value that is (g2/A2)/(q1/A1) (the ratio of the charge-to-mass ratios) times that of the first ions.

In a case of a large difference in the charge-to-mass ratio between the first ion and the second ion, the second accelerating cycle phase difference may be further increased to 2.5 cycles or 3.5 cycles. In this way, the accelerating operation is performed by setting the second accelerating cycle phase difference for accelerating the second ions to be larger than the first accelerating cycle phase difference for accelerating the first ions. Preferably, the first accelerating cycle phase difference may be set to half the cycle (0.5 cycles) and the second accelerating cycle phase difference may be set to (0.5+n) cycles (n: an integer). By thus designing the drift-tube linear accelerator to allow the second ions having a lower charge-to-mass ratio to be injected with an energy lower than the first ions, the difference between the radio frequency power fed to accelerate the first ions and that fed to accelerate the heavier second ions having a charge-to-mass ratio lower than the first ions can be reduced, thereby eliminating the necessity of a large power radio frequency generator.

Conventionally, there has been only a design concept that an accelerating operation is designed first for the heavy second ions having a large mass and a low charge-to-mass ratio (for example, the tetravalent carbon ions) which need a large radio frequency power to accelerate, whereby the light first ions having a small mass and a high charge-to-mass ratio (for example, protons) can be accelerated to the same energy level as the second ions by reducing the radio frequency power. In other words, there has been only a design concept that the first ions and the second ions are accelerated by the operation illustrated in FIG. 4. In this way, the first ions were accelerated to the same energy level as the second ions by reducing the radio frequency power from that for accelerating the second ions. Thus, there has been needed a radio frequency generator that is capable of outputting radio frequency power for accelerating the second ions to the same energy level as the first ions. Nevertheless, the present inventors found that using a radio frequency generator having substantially the same capability of accelerating the light first ions having a high charge-to-mass ratio, the heavy second ions having a low charge-to-mass ratio can be accelerated, although the injection energy is lowered, by setting the second accelerating cycle phase difference to be larger than the first accelerating cycle phase difference, and successfully realized a drift tube linear accelerator that is capable of accelerating the two kinds of ions.

Figure 6:
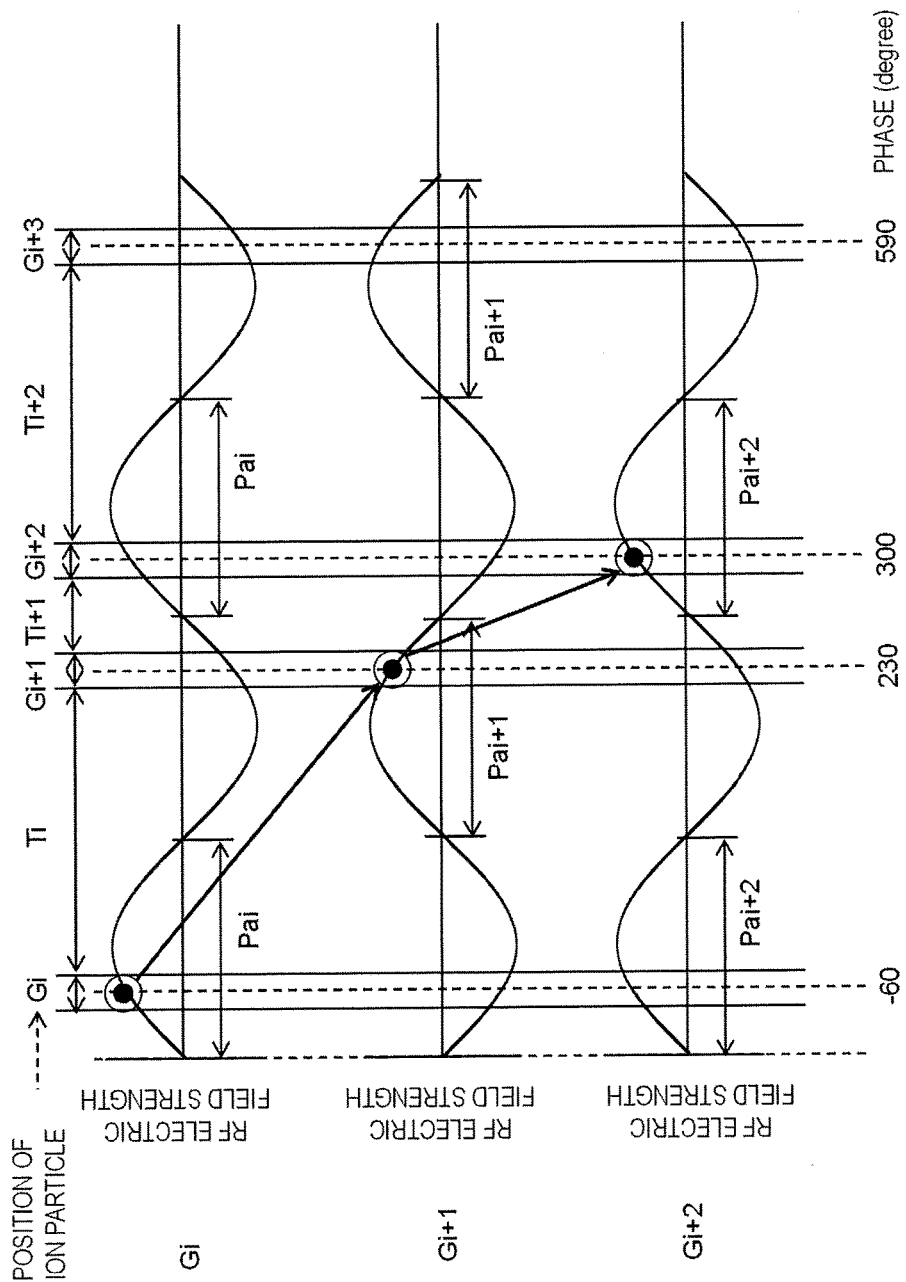
FIG. 6 is a diagrammatic chart illustrating an operation of accelerating the first ions in another drift-tube linear accelerator in the synchrotron injector system according to Embodiment 1 of the present invention.

FIG. 6 is a diagram illustrating an operation of an alternating-phase focusing IH (APF-IH) drift-tube linear accelerator, which is categorized as an IH drift-tube linear accelerator. The APF-IH drift-tube linear accelerator is designed for the ions to pass through the drift tube gap Gi at a phase around −60 degrees, then to pass through the next drift tube gap Gi+1 at a phase around +50 degrees from the peak of the radio frequency electric field, i.e., around 230 degrees, and then to pass through the further next drift tube gap Gi+2 at a phase around −60 degrees from the peak of the radio frequency electric field as with the drift tube gap Gi, i.e., around 300 degrees. This design allows the accelerator to prevent the beam from diverging only by the radio frequency electric fields without being provided with an additional converging device. Similarly to the operation of the IH drift-tube linear accelerator illustrated in FIG. 4, the APF-IH drift-tube linear accelerator is also operated to accelerate the ions in accelerating half cycles whose phase difference between the adjacent drift tube gaps is shifted from each other by half the cycle as illustrated in FIG. 6. In the present invention, the APF-IH drift-tube linear accelerator is designed to perform the operation of accelerating the first ions as illustrated in FIG. 6, and the second ions having a charge-to-mass ratio lower than the first ions are accelerated according to an accelerating operation as illustrated in FIG. 7 using the so designed APF-IH drift-tube linear accelerator.

Figure 7:
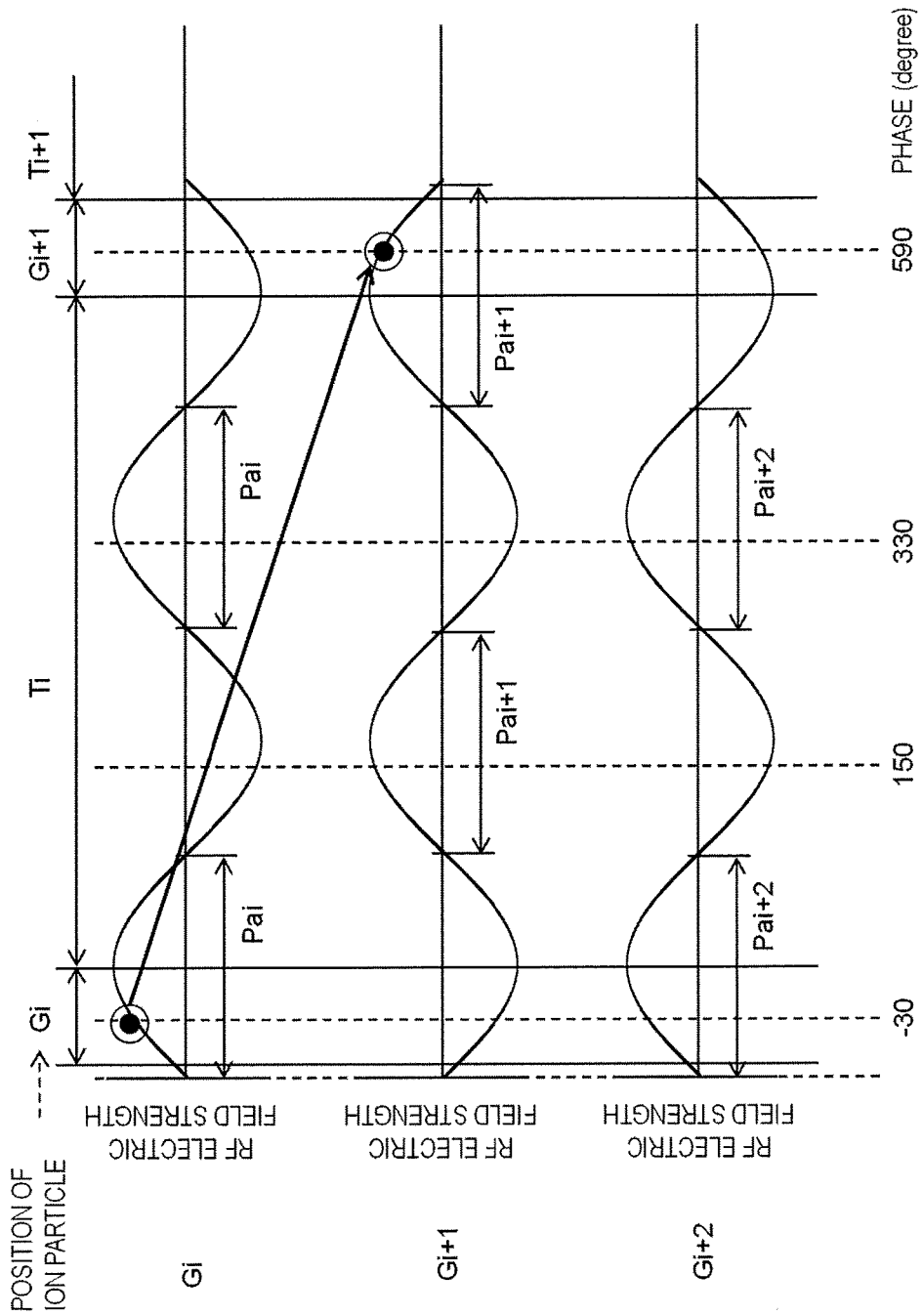
FIG. 7 is a diagrammatic chart illustrating an operation of accelerating the second ions in the other drift-tube linear accelerator in the synchrotron injector system according to Embodiment 1 of the present invention.
Figure 8:
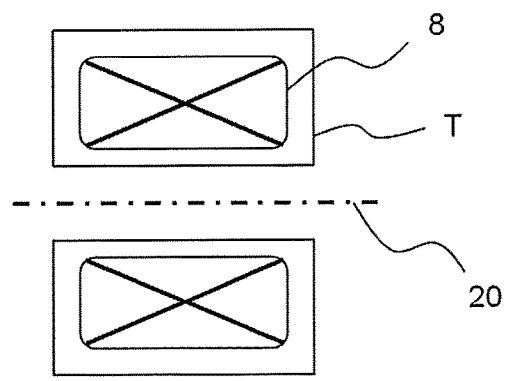
FIG. 8 is a cross-sectional view schematically showing an example of a configuration of the drift tube of the drift tube linear accelerator in the synchrotron injector system according to Embodiment 1 of the present invention.

The bunch of second ions is accelerated while passing through the drift tube gap Gi at a phase around −60 degrees, as shown in FIG. 7. The radio frequency electric field strength, i.e., the radio frequency power fed into the cylindrical resonator is adjusted for the bunch of ions to pass through the drift tube gap Gi+1 at a phase around 590 degrees, i.e., at a phase around +50 degrees from the peak of the radio frequency electric field strength not in the next half cycle but in the accelerating half cycle that is the half cycle further delayed by one cycle from the next half cycle. According to the above operation, the second ions have a lower velocity than the first ions, in other words, have a lower energy when injected from the drift tube linear accelerator, as the operations illustrated in FIGS. 4 and 5. This operation can prevent the first ions from diverging only by the radio frequency electric filed, but in some situations cannot prevent the second ions from diverging only by the radio frequency electric filed. In these situations, a converging device 8 that produces a magnetic field may be incorporated in each of the drift tubes T as shown in FIG. 8 to prevent the divergence by operating the focusing device 8 during acceleration of the second ions.

Figure 9:
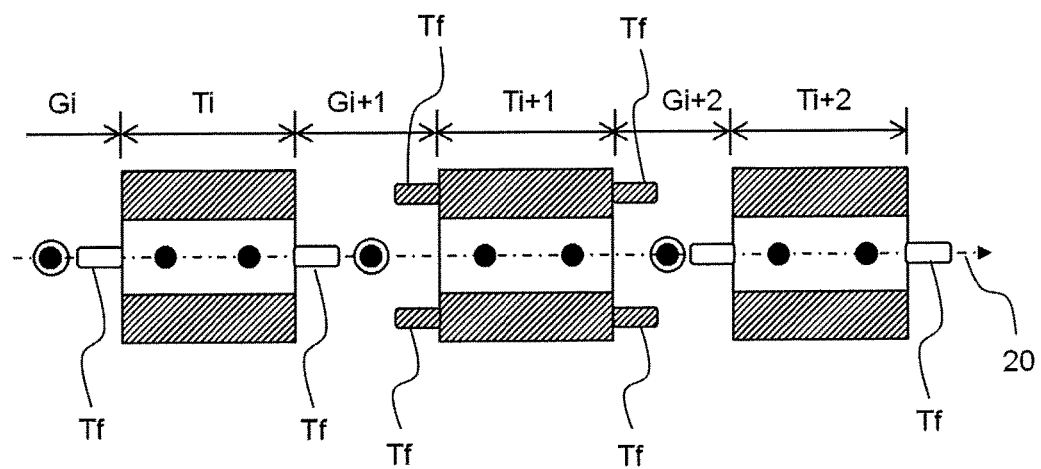
FIG. 9 is a side cross-sectional view schematically showing an example of a configuration of a relevant section of the drift tube linear accelerator in the synchrotron injector system according to Embodiment 1 of the present invention.
Figure 10:
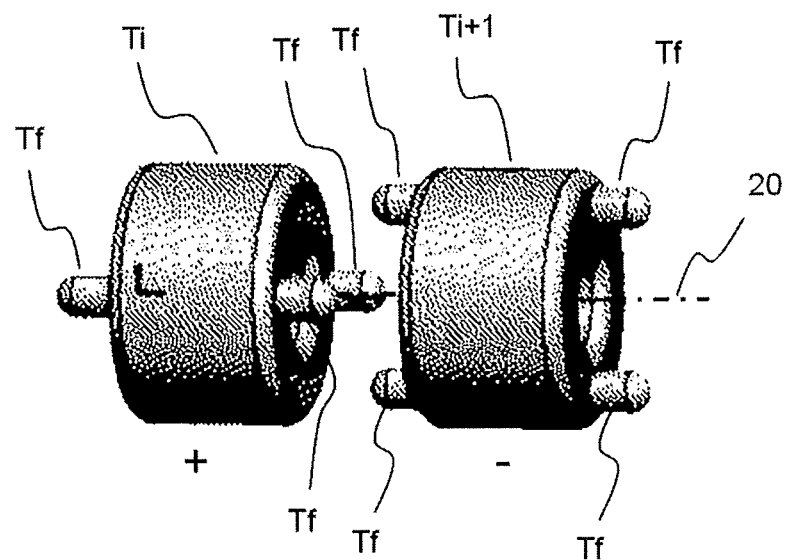
FIG. 10 is a perspective view schematically showing the example of the relevant section of the drift tube linear accelerator in the synchrotron injector system according to Embodiment 1 of the present invention.
Figure 11:
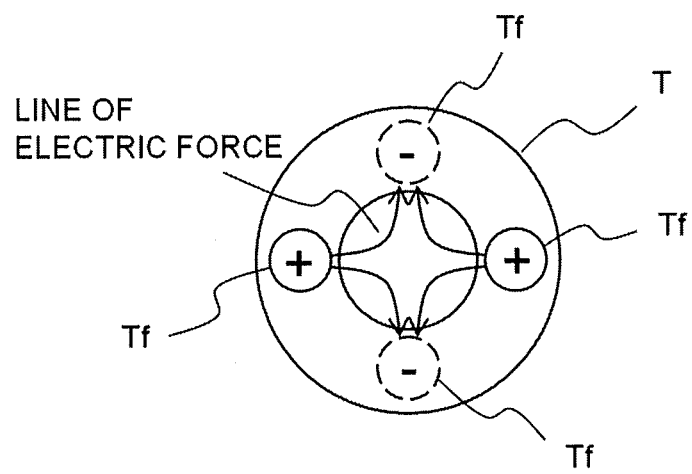
FIG. 11 is diagram illustrating an operation of the FIG. 9 configuration example of the drift tube linear accelerator in the synchrotron injector system according to Embodiment 1 of the present invention.

Furthermore, the divergence can also be prevented by forming the electric fields produced in the drift tube gaps to have a converging capability, as shown in FIGS. 9 to 11. FIG. 9 is a schematic view showing a cross section of the portion ranging from the drift tube Ti to the drift tube Ti+2 among the drift tubes T aligned on the acceleration axis 20; FIG. 10 is a perspective view showing the portion of the drift tube Ti and the drift tube Ti+1; and FIG. 11 is a schematic view of the electric field produced in a drift tube gap, seeing from the acceleration axis. In the configuration shown in FIGS. 9 and 10, the drift-tubes T are respectively provided with finger electrodes Tf projecting toward the gaps. Each electrode Tf is arranged for the radio frequency electric fields produced in the drift tube gaps to form quadrupole electric fields as shown in FIG. 11. For example, two pairs of electrodes Tf may be provided in each drift tube gap, such that the respective electrode pairs projecting from one and the other drift tubes, which form each drift tube gap, are arranged around the acceleration axis 20 at positions different by 90 degrees from each other, as shown in FIGS. 9 and 10. With this arrangement, the quadrupole electric fields are formed in the drift tube gaps, whereby the ions are accelerated while converged. Thus, by appropriately designing the accelerating phase and the to-be-formed quadrupole electric fields for the respective cases of accelerating the first ions and the second ions, either kind of ions can be accelerated without diverging and with suppression of loss. Furthermore, it is possible to combine the converging by the magnetic fields shown in FIG. 8 and the converging by the above-described electric fields.

By thus designing the drift tube linear accelerator to allow the first ions and the second ions to be injected with different energies, the difference between the radio frequency power fed to accelerate the first ions and the radio frequency power fed to accelerate the heavier second ions having a lower charge-to-mass ratio than the first ions can be reduced, thereby eliminating the necessity of a large power radio frequency generator.

The above-described operation of the drift tube linear accelerator in the synchrotron injector system according to Embodiment 1, i.e., the operation of the present invention in the IH drift-tube linear accelerator is summarized below. In the case of accelerating the first ions, the radio frequency power is fed to the drift tube linear accelerator so that the phase difference between the accelerating half cycle for accelerating the first ions in one of the plurality of drift tube gaps and that for accelerating the accelerated first ions reaching the next drift tube gap is set to the first accelerating cycle phase difference. In the case of accelerating the second ions having a charge-to-mass ratio lower than the first ions, the radio frequency power is fed to the drift tube linear accelerator so that the phase difference between the accelerating half cycle for accelerating the second ions in the one drift tube gap and that for accelerating the accelerated second ions reaching the next drift tube gap is set to the second accelerating cycle phase difference that is larger than the first accelerating cycle phase difference. Thus, using a radio frequency generator capable of accelerating the first ions, a synchrotron injector system can be configured that is capable of also accelerating the second ions although the injection energy for the second ions is lower than that for the first ions.

Embodiment 2

Embodiment 2 describes an operation of an Alvarez drift-tube linear accelerator employed as the drift tube linear accelerator 5 constituting the synchrotron injector system 10 shown in FIG. 1. Also in the case of employing the Alvarez drift-tube linear accelerator, by using the radio frequency generator capable of accelerating the first ions for the second ions to be accelerated with an accelerating cycle phase difference larger than that for the first ions, a synchrotron injector system can be configured that is capable of also accelerating the second ions although the second ions are injected with an energy lower than the energy for the first ions.

Figure 12:
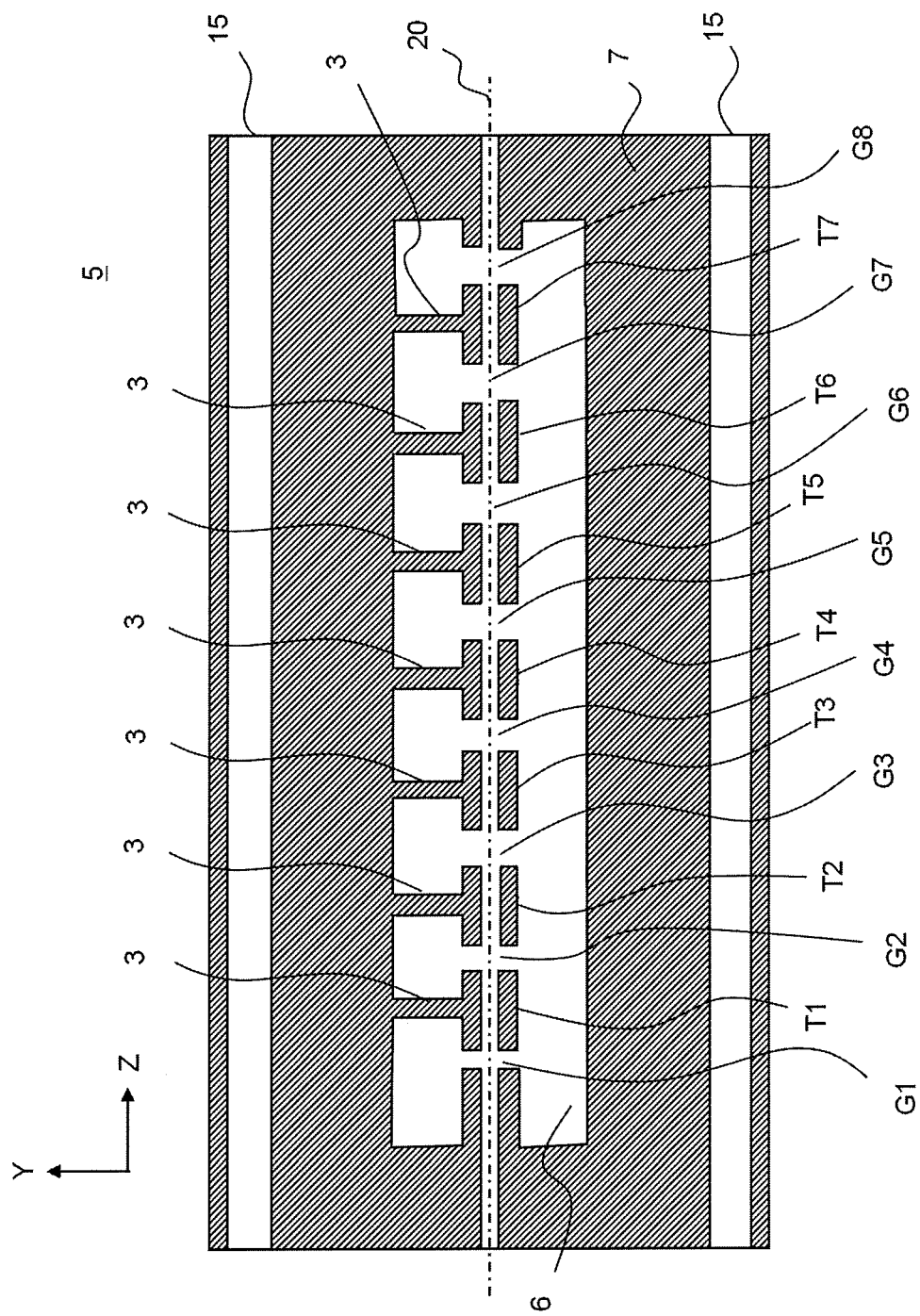
FIG. 12 is a side cross-sectional view schematically showing a configuration of a drift tube linear accelerator in a synchrotron injector system according to Embodiment 2 of the present invention.

FIG. 12 is a side cross-sectional view schematically showing a configuration of a drift tube linear accelerator 5, i.e., an Alvarez drift tube linear accelerator 5 in the synchrotron injector system according to Embodiment 2 of the present invention. The Alvarez drift-tube linear accelerator 5 is also provided with a plurality of drift tubes T1, T2 . . . arranged inside its cylindrical resonator 6 in the cylindrical axial direction thereof. While the arrangement of seven drift tubes is shown in FIG. 12 for simplicity, more drift tubes are arranged in many cases. The inside of the cylindrical resonator 6 is maintained under vacuum. Each drift tube has a cylindrical shape with a center through hole aligned with the acceleration axis 20 along which the ions travel and is supported by a stem 3 fixed to the wall 7 of the cylindrical resonator. In the Alvarez drift-tube linear accelerator, all stems of the drift tubes extend in the same direction. Radio frequency power is fed into the cylindrical resonator from the radio frequency generator 50 shown in FIG. 1 to produce radio frequency electric fields in the adjacent drift tubes gaps G1, G2, . . . . The ions are accelerated by the radio frequency electric fields. In the Alvarez drift-tube linear accelerator, magnetic converging devices are usually incorporated in the drift tubes as shown in FIG. 8 to prevent the beam from diverging in the radial direction. Moreover, the electric field converging illustrated in FIGS. 9 to 11 may be combined.

Figure 13:
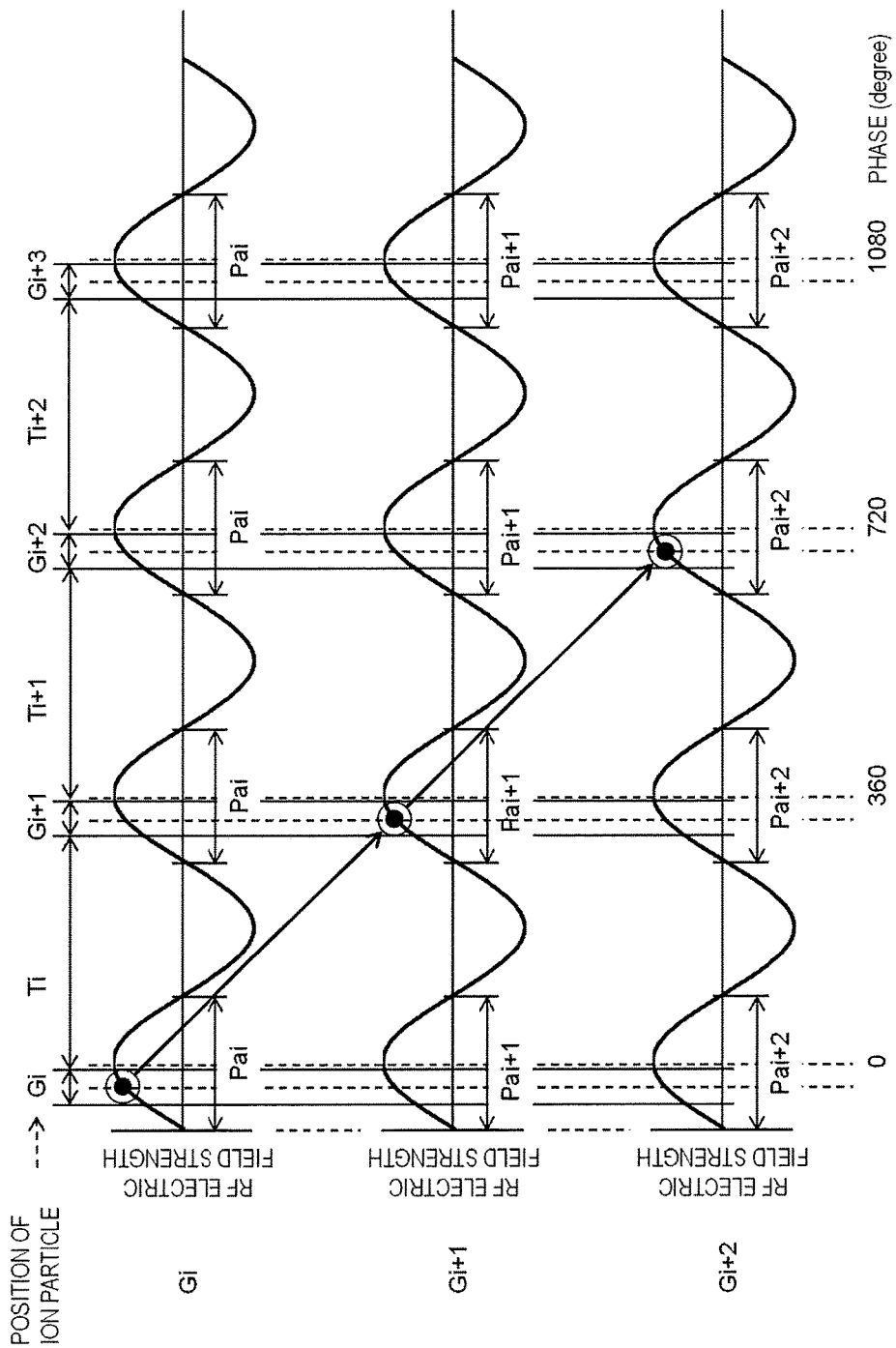
FIG. 13 is a diagrammatic chart illustrating an operation of accelerating the first ions in the drift tube linear accelerator in the synchrotron injector system according to Embodiment 2 of the present invention.

An ion particle accelerating operation of the Alvarez drift-tube linear accelerator is briefly explained with reference to FIG. 13. FIG. 13 is a diagrammatic chart for illustrating how ion particles are accelerated sequentially in the drift tube gaps Gi, Gi+1, Gi+2, . . . while passing therethrough. In FIG. 13, the phase values are written relative to the peak phase of the radio frequency electric field strength produced in the drift tube Gi being defined as 0 degrees. Unlike the IH drift-tube linear accelerator, the Alvarez drift-tube linear accelerator is designed for the radio frequency electric fields produced in adjacent drift tube gaps to have the same phase, as illustrated by the radio frequency electric field strengths in the drift tube gaps Gi, Gi+1 and Gi+1, Gi+2 shown in FIG. 13. Note that in FIG. 13, the radio frequency electric field direction to accelerate the ions is defined to be positive (above each horizontal axes). Since the ions can be accelerated only when the radio frequency electric field strength is positive, the half cycle during the positive radio frequency electric field strength is referred to as an accelerating half cycle as with the case of the IH drift-tube linear accelerator of Embodiment 1. In the Alvarez drift-tube linear accelerator, the phases of the radio frequency are the same in every drift tube gaps; hence, the accelerating half cycle have ranges from (360*N−90) degrees to (360*N+90) degrees, where, the N is an integer including zero.

The double circles represent change in the position of the ion particles as the phase advances, in other words, as time advances, and the arrows represent traveling of the ion particles to the position. The uppermost part of FIG. 13 shows the position of each section of the drift-tube linear accelerator to help indicate in which section the ion particles exist at a phase of the radio frequency, i.e., at a time corresponding to the phase. The ion particles are accelerated in the drift tube gap Gi by receiving energy from the radio frequency electric field produced in the drift tube gap Gi. When the ion particles enter into the drift tube Ti, they are subjected to no acceleration and travel with their energy being kept intact and then further accelerated in the next drift tube gap Gi+1 by receiving energy from the radio frequency electric field produced in the drift tube gap Gi+1. Traveling of the ion particles in this way is illustrated in FIG. 13.

In an Alvarez drift-tube linear accelerator, the electric field strength is typically adjusted for the ion particles to pass through a drift tube gap at a phase shortly before the electric field strength peaks in an accelerating half cycle, for example, at a phase around −30 degrees from the peak of the electric field strength in the drift tube gap Gi as shown in FIG. 13. This forms a bunch of ion particles because ion particles passing a little later through the gap are more accelerated. In the Alvarez drift-tube linear accelerator, since the radio frequency electric field having the same phase is produced in the next drift tube gap, the accelerating half cycle Pai+1 at the drift tube gap Gi+1 is delayed by one cycle from the accelerating half cycle Pai at the drift tube gap Gi. That is, the phase difference between accelerating half cycles at adjacent drift tube gaps is one cycle. The drift tube linear accelerator is designed for the bunch of ions to pass through the drift tube gap Gi+1 a little before the radio frequency electric field strength in the accelerating half cycle reaches its peak, more specifically, at a phase around 150 degrees. In this way, the bunch of ions is accelerated every time it passes through the drift tubes.

A conventional Alvarez drift-tube linear accelerator is designed as described above. During operation, the radio frequency power is fed so that the accelerating operation is performed in accordance with the design to accelerate the bunch of ion particles, i.e., the ion beam, whereby the ion beam having the design energy is injected into the synchrotron 100. In Embodiment 2 of the present invention, the first ions having a high charge-to-mass ratio (for example, the protons) are accelerated by the same operation as with the conventional one illustrated in FIG. 13. The second ions having a low charge-to-mass ratio (for example, the tetravalent carbon ions), however, are accelerated in the accelerating half cycles which phase difference between adjacent drift tube gaps is set larger than the phase difference between the accelerating half cycles for the first ions. As with Embodiment 1, the phase difference between the accelerating half cycles in which the first ions are accelerated is referred to as a first accelerating cycle phase difference and the phase difference between the accelerating half cycles in which the second ions are accelerated is referred to as a second accelerating cycle phase difference. In the above operation, the first accelerating cycle phase difference is one cycle.

Figure 14:
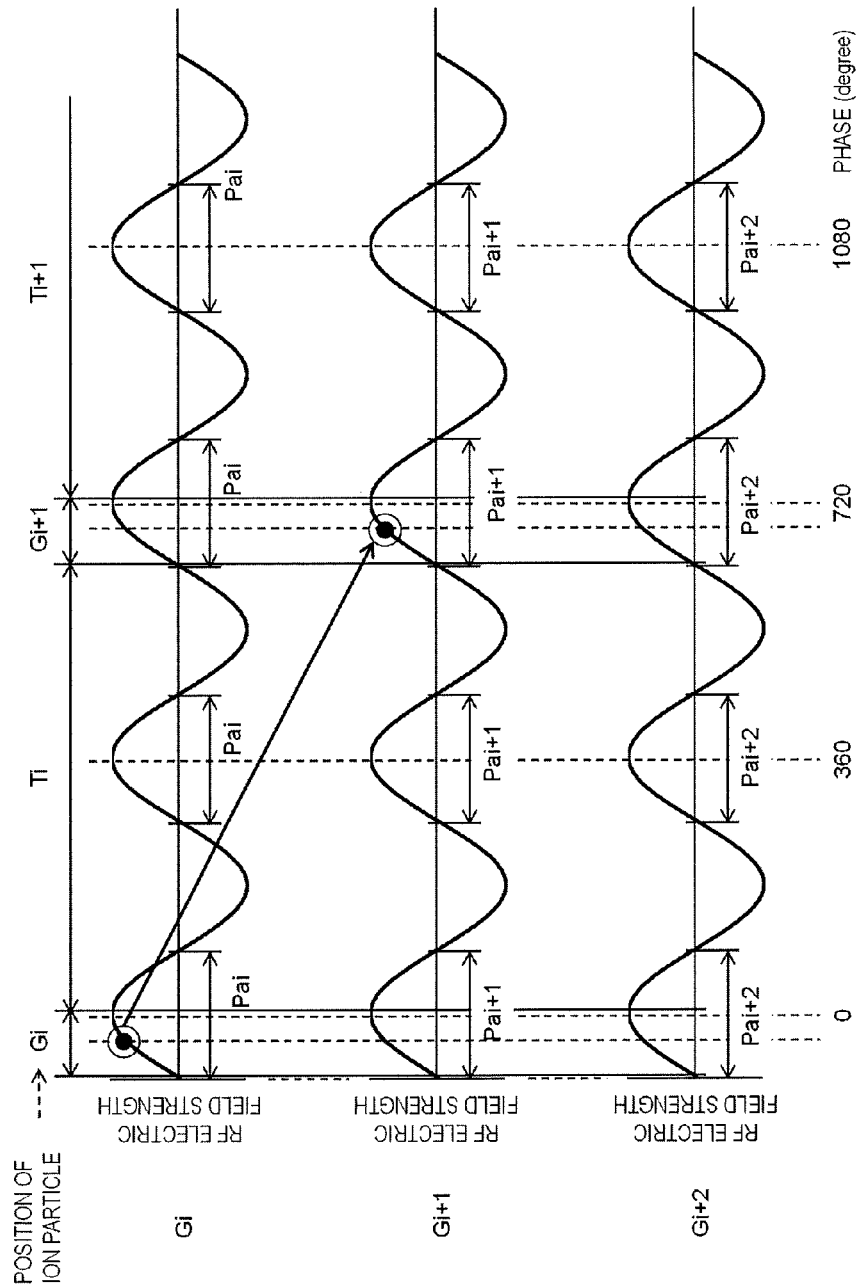
FIG. 14 is a diagrammatic chart illustrating an operation of accelerating the second ions in the drift tube linear accelerator in the synchrotron injector system according to Embodiment 2 of the present invention.

FIG. 14 is a diagram illustrating how the drift tube linear accelerator in the synchrotron injector system according to Embodiment 2 of the present invention, i.e., the Alvarez drift-tube linear accelerator, accelerates the second ions of the tetravalent carbon ions. The bunch of second ions is accelerated when passing through the drift tube gap Gi at a phase shortly before the radio frequency electric field strength peaks. The radio frequency electric field strength, i.e., the radio frequency power fed into the cylindrical resonator, is adjusted so that the ion beam is accelerated in the drift tube gap Gi+1 not at a phase in the next cycle but at a phase shortly before the radio frequency electric field strength peaks in the further next half cycle that is the accelerating half cycle delayed by one cycle from the next cycle. In the above operation, the second accelerating cycle phase difference is two cycles. By such the accelerating operation, the second ions are accelerated to a velocity lower than the first ions. In other words, the energy of the second ions injected from the drift tube linear accelerator is lower than that of the first ions. Representing the charge and mass of the first ion and the charge and mass of the second ion by q1, A1, and q2, A2, respectively, the injection energy of the second ions is preferably set to a value that is (q2/A2)/(q1/A1) (the ratio of the charge-to-mass ratios) times that of the first ions.

In a case of a large difference in the charge-to-mass ratio between the first ion and the second ion, the second accelerating cycle phase difference may be further increased to three cycles or four cycles. In this way, the accelerating operation is performed by setting the second accelerating cycle phase difference for accelerating the second ions to be larger than the first accelerating cycle phase difference for accelerating the first ions. Preferably, the first accelerating cycle phase difference may be set to one cycle and the second accelerating cycle phase difference may be set to (1+n) cycles (n: an integer). By thus designing the Alvarez drift-tube linear accelerator, as with the IH drift-tube linear accelerator, to allow the second ions having a lower charge-to-mass ratio to be injected with an energy lower than the first ions, the difference between the radio frequency power fed to accelerate the first ions and that fed to accelerate the heavier second ions having a charge-to-mass ratio lower than the first ions can be reduced, thereby eliminating the necessity of a large power radio frequency generator.

The above-described operation of the drift tube linear accelerator for a synchrotron injector system according to Embodiment 2, i.e., the operation of the present invention in the Alvarez drift-tube linear accelerator is summarized below as with the operation of the IH drift-tube linear accelerator described in Embodiment 1. In the case of accelerating the first ions, the radio frequency power is fed to the drift tube linear accelerator so that the phase difference between the accelerating half cycle for accelerating the first ions in one of the plurality of drift tube gaps and that for accelerating the accelerated first ions reaching the next drift tube gap is set to the first accelerating cycle phase difference; and in the case of accelerating the second ions having a charge-to-mass ratio lower than the first ions, the radio frequency power is fed to the drift tube linear accelerator so that the phase difference between the accelerating half cycle for accelerating the second ions in the one drift tube gap and that for accelerating the accelerated second ions reaching the next drift tube gap is set to the second accelerating cycle phase difference that is larger than the first accelerating cycle phase difference. Thus, using radio frequency generator capable of accelerating the first ions, a synchrotron injector system can be configured that is capable of also accelerating the second ions although the injection energy for the second ions is lower than that for the first ions.

It should be noted that each embodiment of the present invention may be appropriately modified or omitted within the spirit and the scope of the invention.

NUMERAL REFERENCES

1: first ion source; 2: second ion source; 3: stems; 4: low-energy beam delivery line; 5: drift tube linear accelerator; 6: cylindrical resonator; 8: converging device; 10: synchrotron injector system; 20: acceleration axis; 43: beam line merging device; 50: radio frequency generator; 100: synchrotron; G1 to G7: drift tube gap; T, T1 to T7: drift tube; Pai, Pai+1, Pai+2: accelerating half cycle; and Tf: electrodes.

The invention claimed is:

1. A synchrotron injector system for injecting ions into a synchrotron, comprising:
    a first ion source for generating first ions;
    a second ion source for generating second ions having a charge-to-mass ratio (q2/A2) lower than the charge-to-mass ratio (q1/A1) of the first ions;
    a drift tube linear accelerator including:
        a cylindrical resonator; and
        a plurality of drift tubes arranged linearly along the center axis of the cylindrical resonator, for accelerating ions in an accelerating half cycle that is a radio frequency half cycle containing an accelerating phase of radio frequency electric fields produced in a plurality of drift tube gaps formed between the plurality of drift tubes;
    a radio frequency generator for feeding radio frequency power to the drift tube linear accelerator; and
    a low-energy beam delivery line for injecting either the first ions or the second ions into the drift tube linear accelerator, wherein
    when the first ions are injected from the low-energy beam delivery line, the radio frequency generator feeds the radio frequency power to the drift tube linear accelerator so that the phase difference between an accelerating half cycle for accelerating the first ions in one drift tube gap of the plurality of drift tube gaps and an accelerating half cycle for accelerating the accelerated first ions reaching the next drift tube gap is set to a first accelerating cycle phase difference and
    when the second ions are injected from the low-energy beam delivery line, the radio frequency generator feeds the radio frequency power to the drift tube linear accelerator so that the phase difference between an accelerating half cycle for accelerating the second ions in the one drift tube gap and an accelerating half cycle for the accelerated second ions reaching the next drift tube gap is set to a second accelerating cycle phase difference that is larger than the first accelerating cycle phase difference.

2. The injector system for synchrotron of claim 1, wherein the drift tube linear accelerator is an APF-IH drift-tube linear accelerator, and the first accelerating cycle phase difference is set to 0.5 cycles and the second accelerating cycle phase difference is set to (0.5+n) cycles, where n is a positive integer.

3. The injector system for synchrotron of claim 2, wherein magnetic converging devices are provided in drift tubes.

4. The injector system for synchrotron of claim 1, wherein the drift tube linear accelerator is an Alvarez drift-tube linear accelerator, and the first accelerating cycle phase difference is set to one cycle and the second accelerating cycle phase difference is set to (1+n) cycles, where n is a positive integer.

5. The injector system for synchrotron of claim 1, wherein each drift tube is provided with electrodes projecting in each drift tube gap to form a quadrupole electric field in each drift tube gap.

6. The injector system for synchrotron of claim 1, wherein the first ions are protons and the second ions are tetravalent carbon ions.

7. An operating method for a drift-tube linear accelerator that includes a cylindrical resonator and a plurality of drift tubes arranged linearly along the center axis of the cylindrical resonator, to accelerate either first ions or second ions having a charge-to-mass ratio (q2/A2) lower than the charge-to-mass ratio (q1/A1) of the first ions in an accelerating half cycle that is a radio frequency half cycle containing an accelerating phase of radio frequency electric fields produced in a plurality of drift tube gaps formed between the plurality of drift tubes,
    the operating method for the drift-tube linear accelerator characterized in that the drift-tube linear accelerator operates so that when accelerating the first ions, radio frequency power is fed the radio frequency power to the drift tube linear accelerator so that the phase difference between an accelerating half cycle for accelerating the first ions in one drift tube gap of the plurality of drift tube gaps and an accelerating half cycle for accelerating the accelerated first ions reaching the next drift tube gap is set to a first accelerating cycle phase difference and when accelerating the second ions, the radio frequency power is fed to the drift tube linear accelerator so that the phase difference between an accelerating half cycle for accelerating the second ions in the one drift tube gap and an accelerating half cycle for the accelerated second ions reaching the next drift tube gap is set to a second accelerating cycle phase difference that is larger than the first accelerating cycle phase difference.

8. The operating method for a drift-tube linear accelerator, according to claim 7, wherein the drift tube linear accelerator is an APF-IH linear accelerator, and the first accelerating cycle phase difference is set to 0.5 cycles and the second accelerating cycle phase difference is set to (0.5+n) cycles, where n is a positive integer.

9. The operating method for a drift-tube linear accelerator, according to claim 7, wherein the drift tube linear accelerator is an Alvarez drift-tube linear accelerator, and the first accelerating cycle phase difference is set to one cycle and the second accelerating cycle phase difference is set to (1+n) cycles, where n is a positive integer.

10. The operating method for a drift-tube linear accelerator, according to claim 7, wherein the first ions are protons and the second ions are tetravalent carbon ions.

* * * * *